United States Patent [19]

Choudhury et al.

[11] Patent Number: 5,219,354
[45] Date of Patent: Jun. 15, 1993

[54] DISSECTING-CUM HAEMOSTAPLING SCISSORS

[76] Inventors: Vijay K. Choudhury; Sujata Choudhury, both of 42-2 Telecom Ghat Rly. Colony, Howrah-711 101, West Bengal, India

[21] Appl. No.: 594,148

[22] Filed: Oct. 9, 1990

[51] Int. Cl.⁵ .............................................. A61B 17/32
[52] U.S. Cl. .................................... 606/174; 606/142; 606/205
[58] Field of Search ................. 606/83, 120, 139, 142, 606/143, 157, 158, 167, 174, 205, 206, 207, 208, 209, 210, 211; 30/173, 258, 134; 294/99.2; 227/178, 180, 901, 19

[56] References Cited

U.S. PATENT DOCUMENTS

| | | | |
|---|---|---|---|
| 2,434,831 | 1/1948 | Brandenburg | 606/120 |
| 3,006,344 | 10/1961 | Vogelfanger | 606/174 |
| 3,175,556 | 3/1965 | Wood et al. | 606/174 |
| 4,682,596 | 7/1987 | Beraha | 606/147 |

FOREIGN PATENT DOCUMENTS 8602541  5/1986  World Int. Prop. O. .......... 606/120

Primary Examiner—C. Fred Rosenbaum
Assistant Examiner—William W. Lewis
Attorney, Agent, or Firm—Helfgott & Karas

[57] ABSTRACT

Dissecting cum-haemostapling scissors comprise an upper and lower jaw members having handles provided with cooperating lock elements. The lower jaw member has a longitudinal slit accommodating a pivotable spring-biased cutting blade. When the handles are gradually brought together, haemostatic grooves provided in both members firstly nip tubular blood vessels on either side of the blade, and then the blade cuts the blood vessel. The upper jaw member is also provided with a set of haemostaple pins in a slit housing provided in the upper jaw member. By further operation of the handles, a blunt end of the blade actuates or triggers a haemostapling system which releases a staple from a staple magazine and the staple clasps firmly the severed ends of the blood vessel. The lower jaw member is further provided with an automatic alignment system to align blood vessels with a cutting edge of the blade.

18 Claims, 7 Drawing Sheets

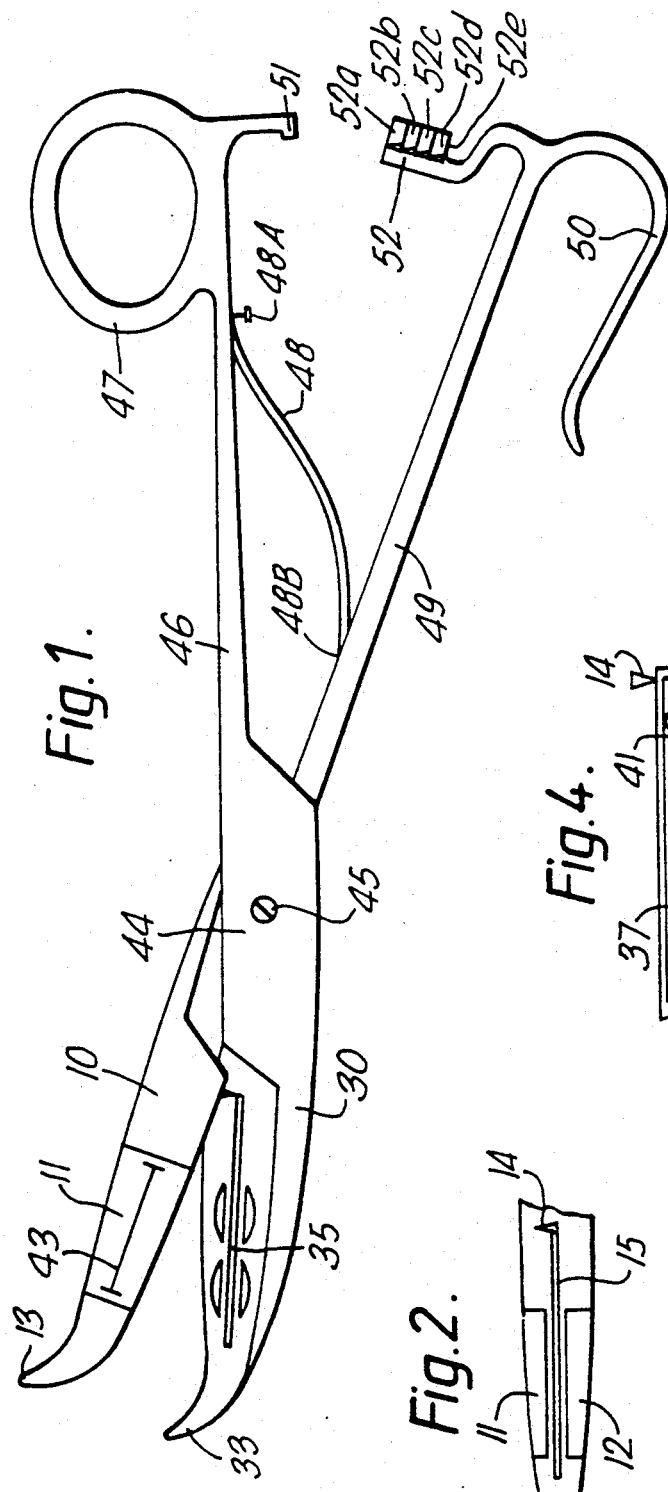

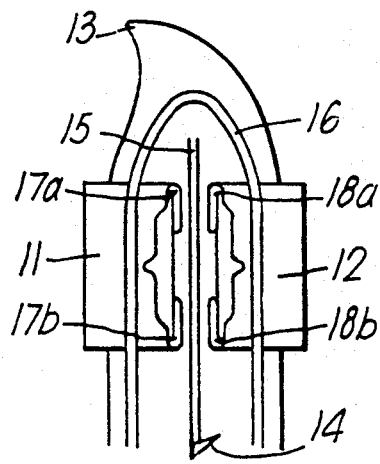
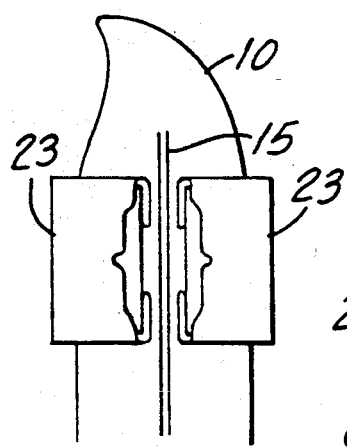
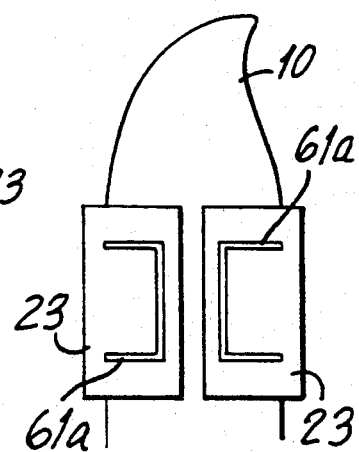
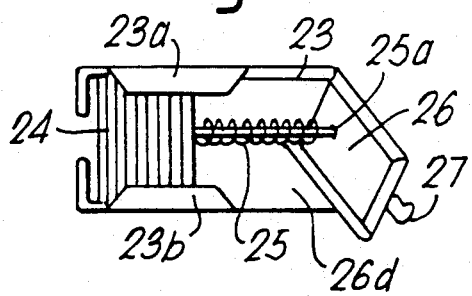
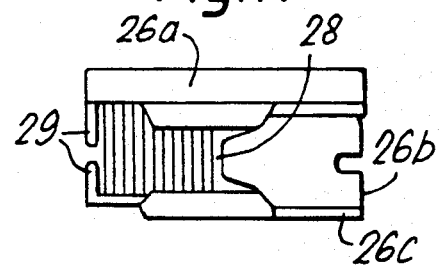
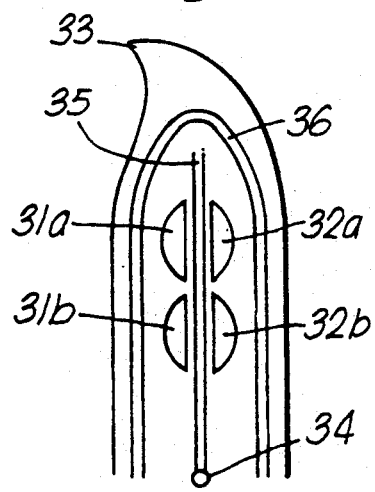
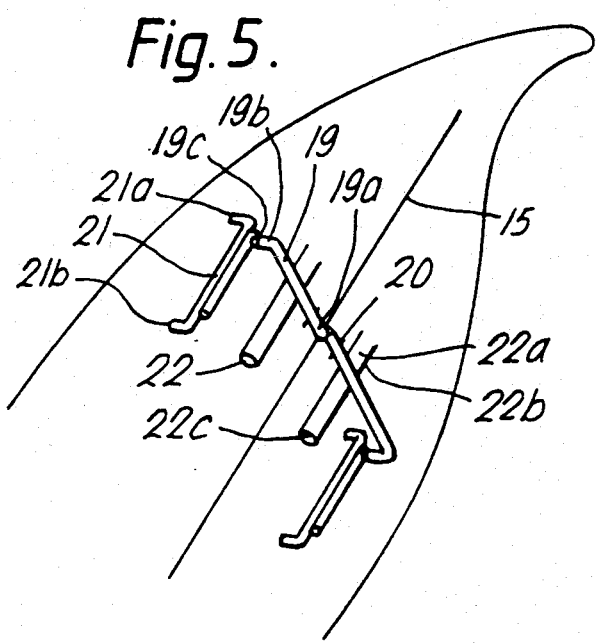

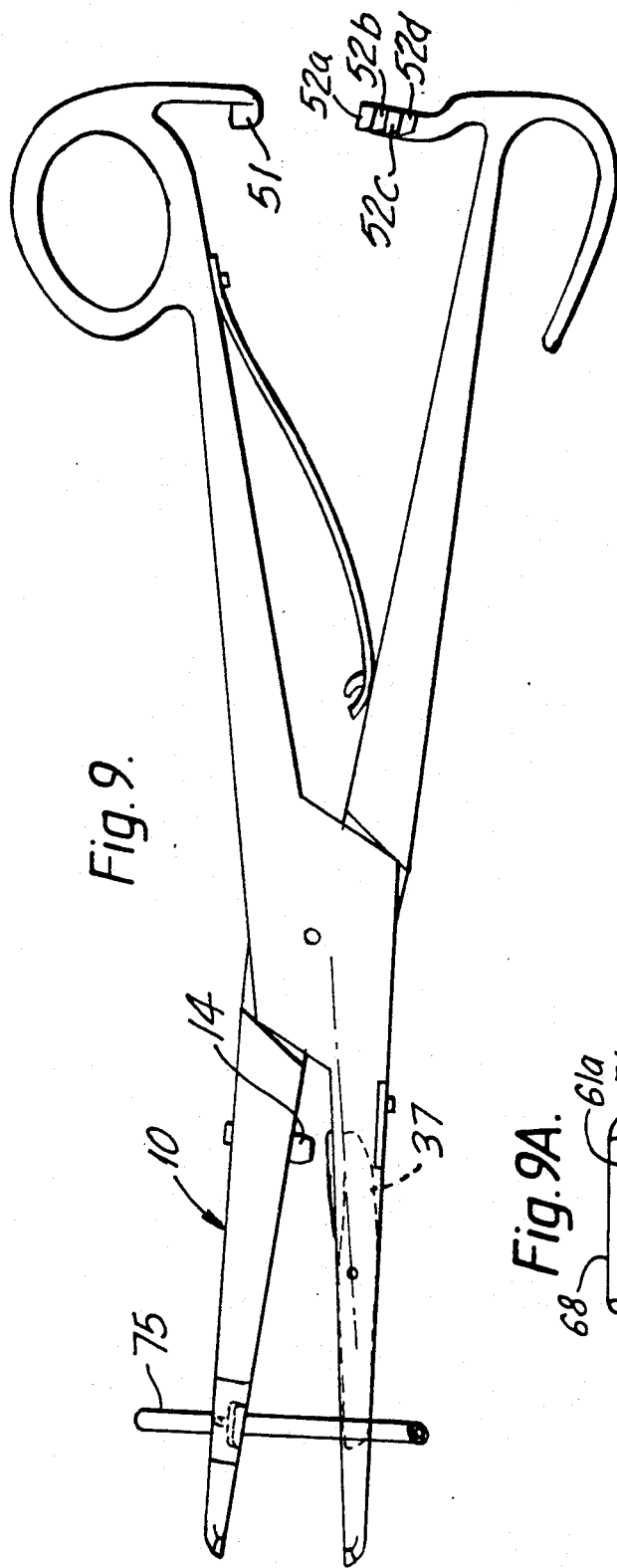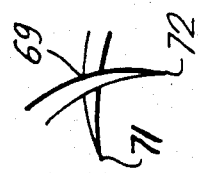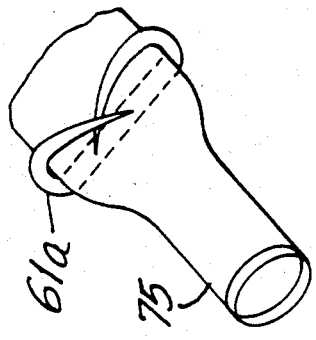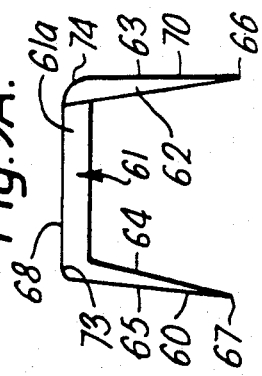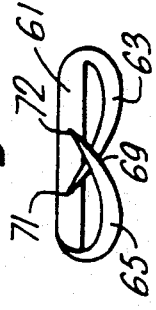

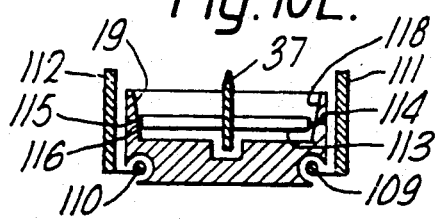
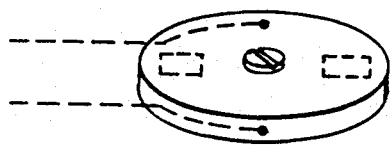
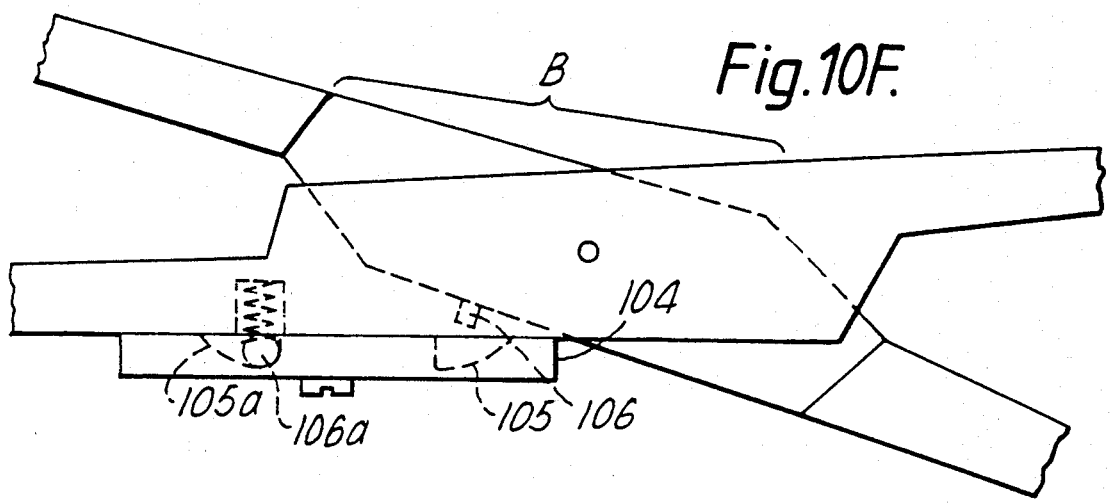
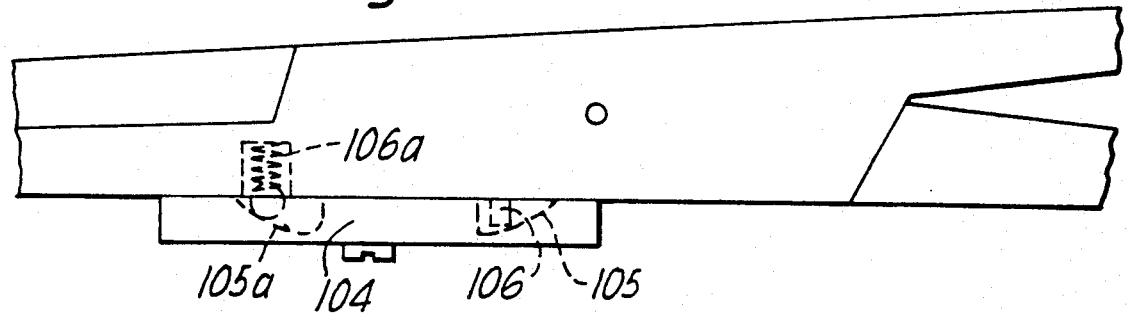
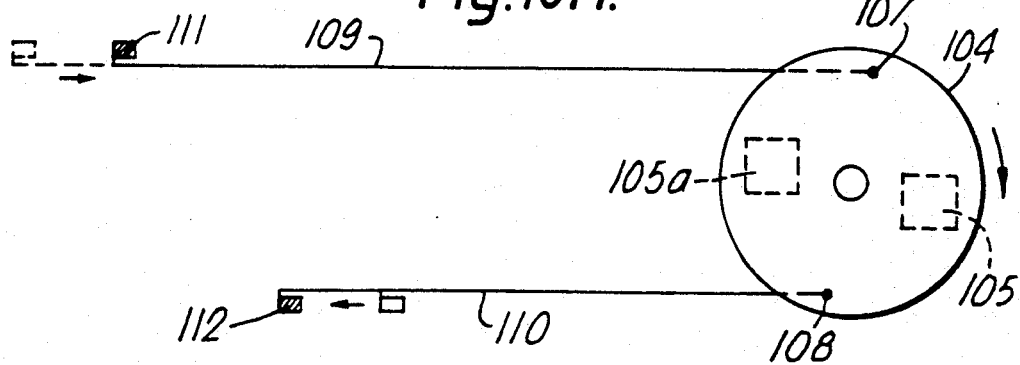

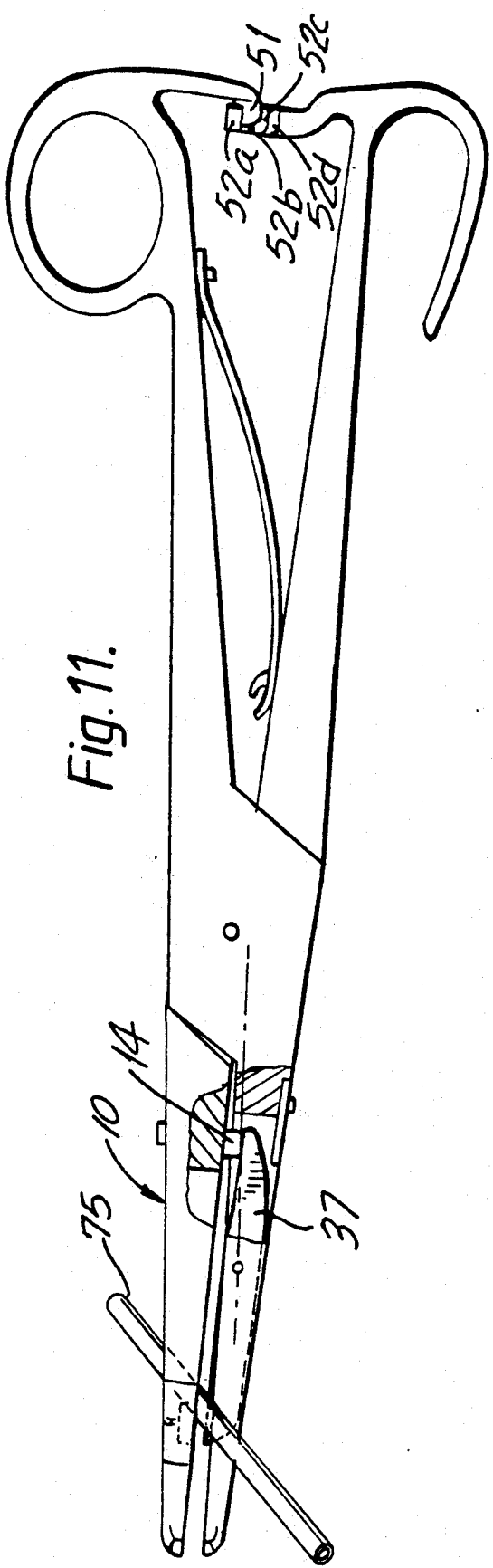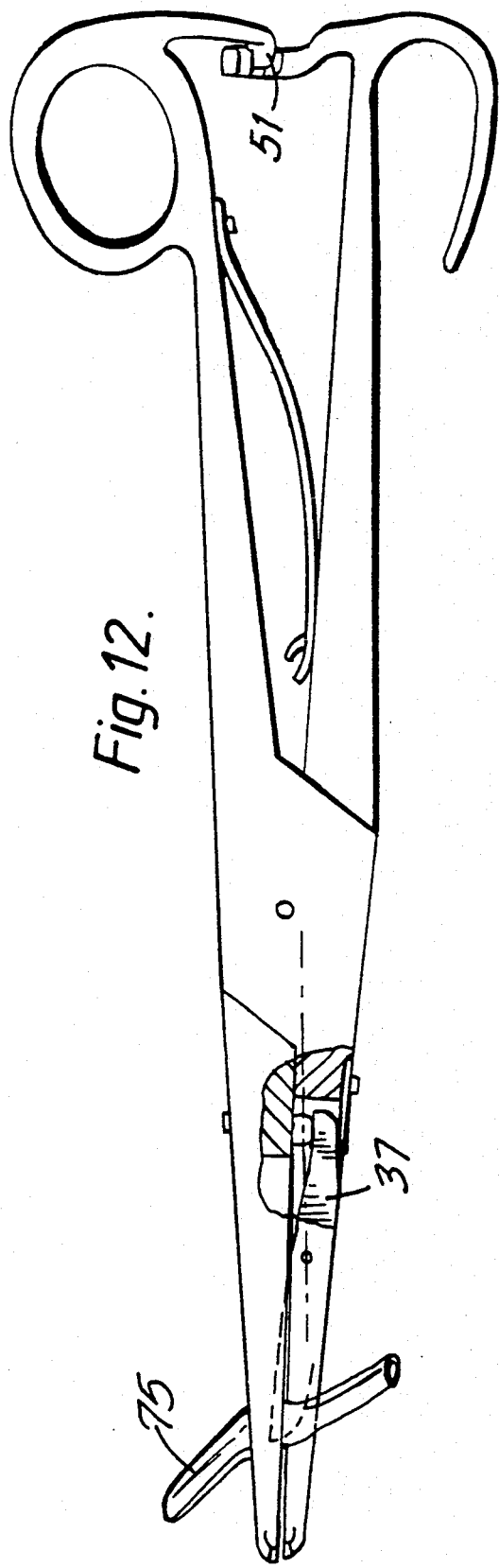

DISSECTING-CUM HAEMOSTAPLING SCISSORS

BACKGROUND OF THE INVENTION

This invention relates to a novel dissecting-cum-haemostapling scissors.

Haemostasis-cutting-ligation or cauterization constitute the basic principle of surgery of vascular tissues, blood vessels or fluid ducts which is carried out in all kinds of operations.

In a conventional technique, before cutting, the vascular tissues or blood vessels are separated adequately from the rest of the tissues by blunt surgery by means of artery forceps, following which haemostasis is ensured by clamping the tissue with the artery forceps at both sides of the line of cut and the tissue is severed by a scissors. Forthwith, the both cut ends of the blood vessels or fluid ducts are ligated with suitable threads or cauterized separately depending upon the caliber of the vessels. Altogether it is a five-step procedure, and it is repeated every now and then during the entire operation which alone consumes nearly one-half of the whole length of operation. In addition, the entire area around the field of surgery remains crowded with numerous artery forceps. The procedure is much more cumbersome therefore for the chief surgeon as well as the assisting surgeons and time consuming especially for oncologists, colo-rectal surgeons, cardiovascular surgeons, neurosurgeons and others. Surgeons often find difficulty in negotiating the vessels when the operating field is deeper and smaller.

Recently, available have been hemoclips produced by Edward Weck Incorporated, U.S.A. and a number of other haemostatic clips and their appliers, as illustrated in U.S. Pat. Nos. 3,867,944; 3,631,707; 3,439,523; 3,439,522; 3,363,628; 3,312,216; 3,270,745 and "Haemostatic Plastic Clip" disclosed in Indian Complete Specification No. 151996; all disclosed devices work on more or less similar principle and technique.

Haemostatic clips used in the devices of aforesaid U.S. Patents and Indian Patent are made up of metal such as aluminum, stainless steel, etc. or absorbable or non-absorbable plastic polymers. U.S. Pat. No. 3,926,195 describes a small, plastic clip designed for temporary or permanent closure of oviduct and vas deferens in humans. The clamping surface of these clips measure from 6 to 10 mm in length and 3 mm to 6 mm in width, which dimensions are larger than those of the clips used as haemostatic clips. Before using these clips, the blood vessel is dissected similarly to the conventional technique by artery forceps and the haemostatic clips are clipped about the vessels at both sides of the line of cut by means of clip appliers. The haemostapled vessels are cut by scissors separately. Henceforth, it is clear that even with the haemoclips the procedure also takes three- steps for executing.

SUMMARY OF THE INVENTION

It is an object of this invention to provide an improved surgical instrument which can achieve the purposes of dissection and haemostapling of blood vessels and fluid ducts.

It is another object of this invention to contrive such an improved surgical device which will be useful for both the blunt dissecting surgery and the sharp cutting surgery with respect to vascular tissues, blood vessels, fluid ducts or any other tissues requiring haemostapling operations.

It is a further object of this invention to provide the single surgical instrument capable of executing the above described procedure with respect to negotiating large numbers of bleeders and spurters that come across during the charted operations easily, effectively and quickly without frequent changing the instruments.

A further object of this invention is to provide the single device which would work like a master surgical instrument to execute a number of small procedures that come across in daily routine surgery as well as specialized charter operations apart from its original novelty of dissecting-cum-haemostapling and cauterization procedure without frequent changing of the instruments, i.e. unlike the present art of surgery in which each and every procedure requires a separate set of instruments and the operating team wastes a considerable amount of time while keeping changing the instruments frequently over for small procedures.

A still further object of this invention is to provide a surgical instrument which will execute a blunt dissection and clamping of tubular vessels at both sides of the line of cut as presently done by two separate artery forceps and wherein cutting will be executed by a concealed disposable blade automatically as done by a scissors in the prior art and wherein cut stumps of the vessels will automatically be clipped by a haemostaple ligation system, so that the blunt dissection-haemostasis cutting-staple ligation and haemocauterization will all be executed in one shot as a single step procedure.

A still further object of this invention is to provide a surgical instrument capable of executing the blunt dissection wherein the dissected blood vessel is brought in an exact alignment of the cutting segment and a haemostapling unit by a built-in automatic aligner, before clamping of tubular vessels at both sides of the line of cut.

Yet another object of this invention is to allow to perform a family planning operation, e.g. vasectomy and tubectomy as a button hole surgery. These operations are executed as one-step procedure using a single instrument of this invention after making a button—hole opening at a desired point in the scotal sack and lower abdomen, respectively. The device of the present invention considerably reduces the operating time and can be used conveniently in the outdoor family planning camps.

According to this invention there is provided a dissecting-cum-haemostatic scissors comprising an upper jaw member and a lower jaw member operatively connected to one another, said upper jaw member having an extension merging into a lower handle member, said lower jaw member having an extension merging into an upper handle member, said upper handle member having a ring portion at its free end adapted to accommodate the thumb of a surgeon, the lower end of said ring having a lock knob adapted to engage a lock release system formed on the upper free end of the lower handle member, said lock release system including a plurality of stages of locks each adapted to engage the lock knob formed at the lower end of the upper handle member when the two handle members are brought closer towards each other, said lock release system also including a lock release member adapted to release the lock knob when the lock knob is brought face to face with said lock release member such that the upper handle member is free from the lower handle member and is released to occupy its original position, a handle spring being provided between said upper handle member and said lower handle member adapted to urge the two handle members to remain separated from each other, the free end of the lower handle member having a support for accommodating the fingers of the surgeon and the upper jaw member extending from said lower handle member being provided with a sharp prong at its extreme forward end.

In the above construction, a set of staple magazines is being accommodated inside the intermediate portion of said upper jaw member, said lower jaw member extending from the upper handle member provided with a sharp prong at its extreme forward end and having a cutting blade accommodated inside a slit housing of the lower jaw member, the arrangement being such that when a vascular tissue or a blood vessel is prepared to be operated upon, the prongs of the jaw members help to receive the vascular tissue or blood vessel between the upper jaw member and the lower jaw member and position the same in the intermediate portion of the scissors directly above the cutting blade and directly below the staple magazine such that when the two jaw members are urged towards each other, not only the vascular tissue or blood vessel is cut but also the cut ends are subjected to haemostapling immediately thereafter automatically. The flat inner surface of the lower jaw member is provided with said longitudinal slit-housing centrally of the same and extending from the inner end of the jaw member to the outer end thereof.

The slit-housing extends downwardly and is adapted to accommodate the sharp blade inside the same with the cutting edge of the blade lying flush with the flat surface of the lower jaw member.

The sharp blade is a disposable blade and has a blunt edged tip disposed towards the outer end of the slit housing and is also provided with a handle member disposed towards the inner end of the slit housing, said handle member of the blade being pivotally secured to the slit-housing by a pivot pin leaving a fulcrum point of the blade handle member, the lower end of the blade handle member being acted upon by a blade-release spring provided within the slit housing, the upper fulcrum point of the blade handle member being acted upon by a fulcrum secured to the inner end of the upper jaw member such that when the two handle members, namely the lower handle member and the upper handle member, are brought towards one another, the upper jaw member and the lower jaw member are urged towards each other and the fulcrum point secured to the inner end of the upper jaw member acts upon the handle member of the blade thereby pivotally urging the blade upwards from the slit-housing while, at the same time, the automatic lock knob comes successively in engagement with the different stages of the lock system.

The inner end of the slit-housing in the lower jaw member is provided with a fulcrum aperture enabling the fulcrum point to enter said aperture and act upon the handle member of the blade, and the lower jaw member is provided with a non-traumatic haemostatic groove surrounding the slit-housing.

The haemostatic groove is in the form of an extended U-shaped groove, the curvature of the U-shaped groove being disposed beyond the outer end of the slit-housing and/or it may be simply parallel to the either side of slit-housing; said slit-housing is provided with a pair of superior staple-clip recesses each being disposed on either side of the slit-housing.

The slit-housing is also provided with a pair of inferior staple clip recesses, each being formed on either side of the slit-housing.

The pair of superior staple clip recesses are provided at the outer end of the slit-housing while the pair of inferior staple clip recesses are provided at the inner end of the slit-housing.

The upper jaw member is centrally provided with a longitudinal slit-housing to accommodate the cutting blade secured in the lower jaw member when the blade is pivotally urged above the surface of the lower jaw member in the instances when the two jaw members are brought closer towards each other.

The slit-housing in the upper jaw member is provided with a pair of staple magazines juxtaposed to each other, one on either side of the slit-housing and in the region directly above the two pairs of staple clip recesses formed on the lower jaw member and, the longitudinal slit-housing in the upper jaw member is also provided with a U-shaped non-traumatic haemostatic groove corresponding to the haemostatic groove formed in the lower jaw member.

Each of the two staple magazines is provided with a plurality of staples having a superior haemostaple leg member and an inferior haemostaple leg member, the superior leg members being provided towards the outer end in the magazine while the inferior leg members are provided towards the proximal end of the magazine, and the two staple magazines are provided with corresponding exits for superior leg members and inferior leg members of the haemostaples.

The staple magazines are provided with a set of haemostaples which are urged by means of a spring of the staple magazine accommodated on a centrally disposed spring bar, and each staple magazine is provided with a lid, and the set of staples or clips rests against a guide member for the haemostaples. When the staple magazines are juxtaposed to each other, one on either side of the slit-housing in the upper jaw member, guide members in the staple magazines are positioned close to said slit-housing in a juxtaposed manner.

A staple trigger member is provided for each of the two staple magazines, each staple trigger member having a blade-acting edge and a haemo-staple acting edge, said staple trigger member being pivotally secured to the upper jaw member close to said blade acting edge and the blade acting edges of the two staple trigger members being positioned in line with the slit-housing in a slightly overlapped manner. The overlapping is arranged in the region where the blunt tip of the blade will enter the slit-housing in the upper jaw member.

The haemo-staple acting edge of the staple trigger member is provided with a staple-plate which rests on the central body of the haemo-staple connecting the superior and inferior leg members, and the underside of the haemo-staple acting edge of the staple trigger member is provided with a staple trigger spring adapted to urge the haemo-staple acting edge upwards so as to effect a withdrawal of the staple plate from urging the haemo-staple pin through the staple exits.

The staple trigger spring is provided with a first leg member resting on the under surface of the upper jaw member and a second leg member resting on the under surface of the edge of the staple trigger member, and the staple trigger member, its associated pivoting pin, the staple trigger spring, staple plate are all provided within a flat undercut in the upper jaw member, such that all protruding edges are flush with the under surface of the upper jaw member.

The staple magazines are provided externally on the upper jaw surface while the staple exits are provided as through slits in the body of the upper jaw member, each slit being disposed on either side of the central or longitudinal axis of the upper jaw member, and the staple magazine spring is provided with a staple or clip fastener adapted to urge the haemo-staple towards the staple guide member.

The staple magazines are provided with a staple clip indicator adapted to help in the process of aligning the blood vessels on the sharp edge of the cutting blade and within the region of the staple magazines.

The handle spring is a leaf spring with one end held to the under surface of either of the upper handle member or lower handle member while its other end is slideably engaged on the other handle member and the slideable end of the handle spring is provided with an indentation at its edge which will slideably engage a groove on the inner surface of the handle member.

In this embodiment the handle spring is made of two leaf plate members, one end of each being secured to one of the two handle members while the free ends of the two spring members are in a sliding contact with each other. In a modified construction, the blade is pivotally held on a hollow mounting bar, the two ends of the mounting bar being provided with two locking members urged by one or more springs held within the hollow of the bar, the two locking members being adapted to engage a hole each on the lateral side of the groove of the lower jaw member, and said blade housing being provided with a further housing portion to accommodate said hollow bar.

By adapting the device for use without a staple magazine, smaller vascular tissues or blood vessels which do not require any ligation, can be cauterized in the usual manner. In the existing practice of cauterization of small blood vessels or tissues, the surgical forceps is connected to a low voltage source by means of a bipolar electrode or standard electro-cauterization unit held by a nurse who makes surface contact between the bipolar electrode or electrocauterization unit and surgical forceps. The operating surgeon simultaneously operates a foot pedal switch completing the circuit thereby enabling the low voltage current to flow through the forceps and cauterization of the vessel is achieved.

Applicants have eliminated the necessity of help of a nurse by modifying the haemostatic cutting process in such a way that a small holding unit such as a socket is made in the surgical forceps at any suitable location such as the finger grip. The bipolar electrode is formed as a detachable plug of a suitable size and shape to fit into the socket. The bipolar electrode is removably fixed to a chord which is removably connected to the cauterization unit. As the operation is in progress, when cauterization is needed, the foot pedal switch of the cauterization unit is operated by the surgeon.

The invention will now be more fully described with reference to the accompanying drawings which illustrate the various constructional features of the invention.

BRIEF DESCRIPTION OF THE DRAWINGS

FIG. 1 is a perspective view of an illustrative embodiment of the dissecting-haemostatic-cutting-haemostapling scissors of the present invention;

FIG. 2 is a plan view of parts of an upper jaw member of the scissors of FIG. 1;

FIGS. 2A is a partial side view of an upper jaw member, illustrating haemostatic components and components of a staple ligation system;

FIG. 2B is a partial side view of the upper jaw member, illustrating only the components of the staple ligation system;

FIG. 2C is a plan view of an upper jaw member of the scissors of FIG. 1;

FIG. 3 is a plan view of a lower jaw of the scissors shown in FIG. 1;

FIG. 3A is a partial plan view of the lower jaw member, depicting a haemostatic groove and components of the staple ligation system;

FIG. 4 is a partial side view of the lower jaw member, showing a cutting device of the scissors of FIG. 1;

FIG. 4A is a side view of a disposable blade, showing the accurate location of a sharp cutting edge and a blunt edge at the tip of the blade;

FIG. 4B is a schematic side view of a spring;

FIG. 5 is a schematic perspective view of components of the staple ligation system provided inside the upper jaw member;

FIG. 6 is a perspective view of an embodiment of a staple magazine containing a clip or staple set, with an opened lid in the position for loading the staple magazine;

FIG. 7 is a plan view of the staple magazine, with a spring-biased lid in the position after loading;

FIG. 8A is a perspective anterior view of an automatic lock-release system;

FIG. 8B is a posterior view of the system of FIG. 8A;

FIG. 9 is a plan view of the upper and lower jaw member, showing the cutting device with the jaws of the scissors in an open position;

FIG. 9A is a front view of a staple clip or haemoclip or haemostaple;

FIG. 9B is a view of the staple-clip of FIG. 9A in operation;

FIG. 9C is a perspective view of leg members of the staple-clip when they clasp about the blood vessel;

FIG. 9D is a plan view of tips of the leg members, showing the leg members in engaged position to lock each other;

FIG. 10E shows a cross-sectional view of the scissors of FIG. 10A;

FIG. 10F shows in detail a portion of the scissors of FIG. 10D in the position in which the jaw members are open;

FIG. 10G shows a portion of the device of FIG. 10D in detail in the position in which the jaw members are in contact with each other;

FIG. 10H is a schematic view of a disc used for the automatic alignment of blood vessels;

FIG. 10I is a perspective view of the disc according to the another embodiment;

FIG. 11 is a top plan view of the scissors in the position in which the blood vessel is nipped thereby;

FIG. 12 is a top plan view of the scissors in the position in which the ends of the blood vessel are severed.

DESCRIPTION OF PREFERRED EMBODIMENTS

Figure 10A:
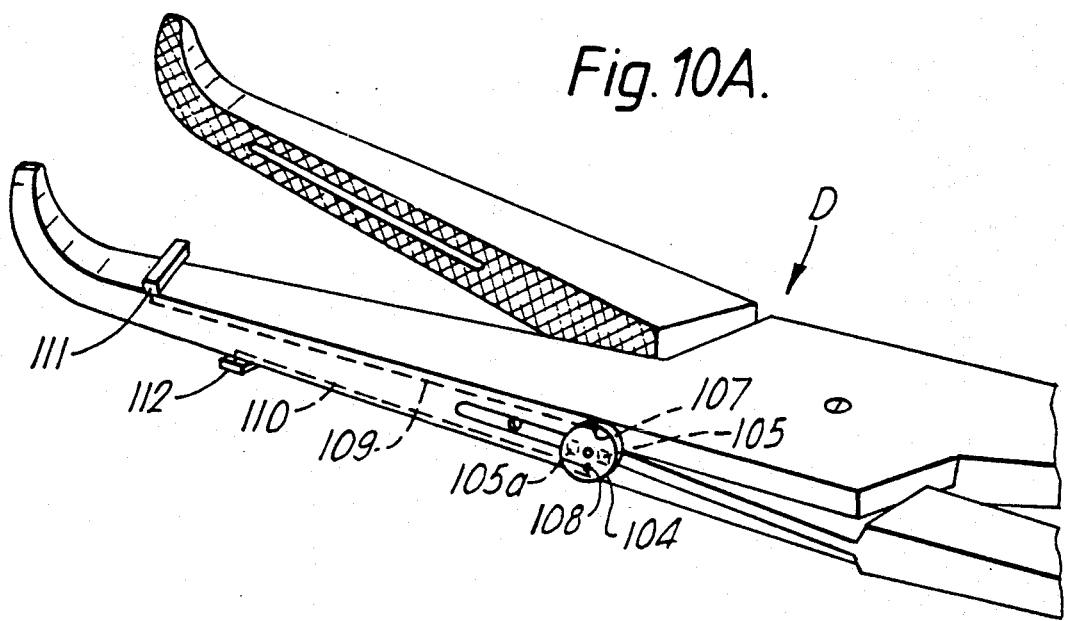
FIG. 10A is a perspective view of the scissors of the invention along with an automatic blood vessel aligner mounted on the underside of the lower jaw member.

Referring now to FIG. 1 of the drawings, a dissecting-cum haemostapling scissors illustrated is more or less like a curved artery forcep, and is comprised of two handle members, an upper handle member 46 and a lower handle member 49 crossing each other at a box joint 44 being fixed at a hinge 45 and maintained to be in an open state, status quo, by a spring 48. The upper end of spring 48 remains fixed with a rivet 48A on the inner surface of upper handle member 46 while the lower end 48B is relatively free to roll in a narrow groove located in the inner surface of lower handle member 49. Handle member 46 extends forward beyond hinge 45 forming serrated lower jaw member 30 while similar extension of handle member 49 forms serrated upper jaw member 10. Hinge 45 constitutes a lever system for both jaw members 10 and 30 with respect to handle members 46 and 49, respectively.

The surgeon normally engages a loop 47 in the upper handle member 46 with his thumb and a curved portion 50 of the lower handle member 49 by his fingers. By pressing the handle members towards each other against the action of spring 48, jaw members 10 and 30 move towards each other and an engaging knob 51 is engaged by locks or ratchets 52a to 52e, depending on the level of operating the handle members. When knob 51 reaches the end of lock 52e, it slips over the same along the posterior surface. As the pressure is released by the surgeon spring 48 acts to separate the handle members from each other and the jaw members open.

i) Dissection Unit

Dissecting unit of this invention as illustrated in FIG. 1 provides that the tip of each of the serrated jaw members 10 and 30 is extended at an obtuse angle to contrive semi-sharp prongs 13 and 33, respectively perpendicular to the major axis of jaw members 10 & 30. Prongs 13 and 33 move inwardly and outwardly relative to hinge 45 and are used for blunt dissection of blood vessels or fluid ducts while separating it from the rest of the tissues.

II) Haemostatic Unit

FIG. 3A illustrates a non-traumatic haemostatic groove 36 located on the flat surface of lower jaw member 30. Groove 36 is formed as a uniformly linear recess of inverted U-shape or may be formed by straight lines parallel to each other formed at either sides of the blade. Groove 36 fits in the similar ridge and recess of a non-traumatic haemostatic groove 16 built into the upper jaw member 10 (FIG. 2A) so that the ridge and recess of haemostatic grooves 36 and 16 remain interlocked while ensuring a complete occlusion of lumen of a tubular vessel or fluid duct lying stretched at both sides of the haemo-staple-recesses when the jaw members 10 and 30 are engaged by approximating handle members 46 and 49 held by the surgeon's thumb inserted into ring 47 and the middle and ring fingers of the surgeon are inserted in the support 50. FIG. 1 also illustrates the automatic lock-release system 52 and 51 which is formed as a proximal extension of handle members 49 and 46, respectively. The system includes an extension 52 which is a somewhat rectangular block, the anterior surface of which has four locks or ratchets 52a, 52b, 52c and 52d mentioned hereinabove, each of which is composed of an offset ledge of that surface and which constitute four locks, respectively, when engaged in sequence by the lock knob 51 as best illustrated in FIG. 8A. The automatic lock-release system may have a plane anterior surface devoid of any ratchets, nevertheless such a lock release system would be similar in operation to that described above. The last offset ledge 52e is designed to have a smooth slope inferiorly continued towards the posterior side of the extension 52 illustrated in FIG. 8B. The last offset ledge is engaged with and disengaged from knob 51 to form the 4th lock, whereupon knob 51 returns upwards to its original position, in situ, while tracking along the posterior surface 52e by virtue of tension of spring 48.

III) Cutting Unit

The cutting unit of the present invention illustrated in FIG. 4 is positioned in jaw member 30 which houses a disposable blade 37 in its slit housing 35. The latter may be a 0.7 mm wide×2 mm deep slit recess extending along the longitudinal axis of the jaw member 30 proximally from a fulcrum aperture 34. Its distal extension is 2 mm beyond recesses 31a, 32b and remains parallel to recesses 31a, 31b at the left side and recesses 32a and 32b at the right side. The disposable blade 37 is made of stainless steel or carbon steel and extends in the longitudinal direction of jaw member 30. Blade 37 resembles more or less a knife with a short handle 40 (FIG. 4A). It may be about 0.5 mm thick and 1.5 mm wide lying erect in the longitudinal plane inside the slit-housing 35 and has a cutting edge 39 and is flush with the flat surface of the jaw member 30. A tip 38 and handle 40 of the blade 37 are made blunt while a remaining portion of the blade constitutes the sharp cutting edge 39 as illustrated in FIG. 4A. The blade 37 has a hole 41a situated in the handle 40 which remains engaged in a lever or pivot pin 41. The latter constitutes the lever mechanism for the blade 37 with respect to handle 40. The jaw member 30 has a cylindrical hole, for example of 2 mm diameter×3 mm deep underneath the pivot pin 41 which houses a spring 42 therein so that handle 40 floats on spring 42 illustrated in FIGS. 4 and 4B similarly to the slit-housing 35 in the lower jaw member 30. The upper jaw member 10 also incorporates a slit-housing 15 which is precisely a mirror image of slit-housing 35 built in jaw 30. The dimensions mentioned herein may vary in accordance with the required size of the instrument. The proximal end of slit-housing 15 has a lug 14 which constitutes the fulcrum for the lever mechanism of blade 37 and it is situated in exact opposition to fulcrum aperture 34 in order to press handle 40 at a point 40a (which is pivoted into pin 41). As a result, blade 37 from its resting position in slit-housing 35 rotates upwards in slit-housing 15 while edge 39 slits any tubular vessels or tissues caught between grooves 36 and 16 of the jaw members 30 and 10 respectively, as best illustrated in FIG. 9. The jaw members 30 & 10 open spontaneously within seconds as soon as knob 51 unlocks the 4th lock after disengaging ledge 52d. Forthwith, the compressed spring 42 is released and spontaneously pushes the handle 40 upwards, whereupon the blade 37 returns, in situ, into slit-housing 35 as illustrated in FIG. 4.

IV) Haemostapling Device

A perspective view of the haemostapling or staple ligation device is illustrated in FIG. 5, and is contrived in the jaw member 10 so that it is placed at the sides of slit-housing 15. The device is again based on a lever mechanism and consists of staple-triggers 19 pivoted on pivot pins 20, about 1.5 mm laterally to the slit-housing 15 at either side so that each trigger 19 engages one end of an open spring 22a and 22b.

The longer arms of triggers 19 rest on the end 22a of spring 22. By virtue of this arrangement, the two triggers 19 remain in a horizontal suspended position. The proximal ends 19a of triggers 19 overlap each other as seen in FIG. 5.

The distal ends 19b of triggers 19 are bent downwards at 90° and each has a staple plate 19c. The blunt tip of blade 37 coincides with the contact point of triggers 19, at the center of the upper jaw. As the blunt tip of the blade strikes ends 19a of triggers 19, their distal ends 19b are further pushed downwards. Ends 19b rest on the haemostaple pin 21 which is pressed towards the cut ends of the blood vessel nipped by the serrated surfaces of the jaw members.

The stages of the stapling operation are shown in FIGS. 9,9B,9C and 9D. Due to matching recesses 31a,31b (FIG. 3A) formed in the surface of the lower jaw member, the free ends of the haemostaple pins are bent thereby stapling the cut ends of the blood vessels as shown in FIG. 9C. The staple trigger 19 is placed perpendicular to the major axis of slit-housing 15 and is about 1 mm thick and 35 mm long. The medial extension of end 19a occupies full width of slit-housing 15 while the other end of trigger 19 bends downwards (90°) perpendicular to its axis of elongation at 19b and remains fixed to staple plate 19c. Numeral 22 denotes a spring which is located laterally of a haemo-staple guide 29. Spring 22 is composed of two leg members 22a and 22b. The leg member 22a becomes coiled at a body 22c and projects outwardly to form the leg member 22b. Forthwith, both leg members provide spring tension to deflect the trigger end 19b upwards while disengaging plate 19c from a staple or clip 61a.

A staple-magazine 23 which fits, into a chamber provided in the jaw member 10 at either sides of the slit-housing resembles a box as best illustrated in FIG. 2C (top view) while FIGS. 2A and 2B show other views of the magazine. The detailed perspective view of magazine 23 is best seen in FIG. 6. Magazine 23 is box-shaped, closed from all sides except the upper side. Surfaces 26a,26b and 26c constitute the posterior, lateral and anterior walls, respectively. Inferior surface 26d constitutes the floor of magazine 23 which bends upwards. A medial wall of the box-like magazine extends only in the middle half of the magazine up to one-half of the height of magazine 23 to form a lug 26e while both sides of the most proximal part of floor 26d are free providing 1 mm gap between the staple guide 29 medially and the lug 26e laterally for the exit of haemostaples. A spring bar 25a is provided, which is connected to the lug and is laterally connected to the lateral wall 26b. The spring bar 25a passes through a staple-clip fastener 28 which is composed of two leg members between anterior wall 26c and posterior wall 26a of magazine 23, so that it can slide medially and laterally along walls 26c and 26a while loading a haemo-staple set 24 in magazine 23. A spring 25 coils around the spring bar 25a in such a fashion that spring bar 25a passes through the internal lumen of spring 25 and extends between lateral wall 26b and fastener 28 proximally. Consequently, tension of spring 25 maintains constant exerting pressure on the set of the haemostaple set 24 towards guide 29. Magazine 23 is open and closed by lid 26 after loading the staple set 24 thereinto; lid 26 fits snug with fastener 28. A lid-hook 27 helps in a pull-it-open operation while lid 26 slides laterally of walls 23a and 23b.

In operation, trigger 19 and plate 19c are adjusted in a linear alignment so that plate 19c thrushes snug over the back of the most proximal staple of set 24 when tip 38 of blade 37 triggers the end 19a to rotate upwards. Consequently, the downward rotation of plate 19c thrushes the most proximal haemostaple to disengage from set 24 to exit downwards.

FIG. 2A illustrates the staple magazines in a plan view and shows staple-magazines 11 and 12 which are fixed snug in their respective chambers designed at both sides of slit-housing 15. Numerals 17a,18a and 17b,18b are sides which constitute gaps for the exits for upper and lower leg members 60,70 of the haemo-staple (shown in FIG. 9A), respectively at both sides. The gap spaced between 17a and 17b and similarly between 18a and 18b form the exit for the body 68 of staple 61A. Jaw member 30 incorporates haemo-staple recesses 31a and 31b for the left side of haemo-staple 61a, designed to be in exact opposition to points 18a and 18b, respectively so as to correspond to leg members 60 and 70 of staple 61A. Similarly, recesses 32a and 32b remain in exact opposition to exit points 17a and 17b respectively to shape the haemo-staple as illustrated in FIG. 9b.

An individual haemo-staple is illustrated in FIG. 9A and has two leg members 60 and 70 which are bent perpendicularly at 73 and 74, respectively from the haemostapling body 61a. 62 defines the vessel-side-face of the leg member 70 while 63 is the outer surface and 66 denotes the pointed tip. Similarly, 64 designates a vessel-side-face of leg member 60 while 65 is the outer surface and 67 is the pointed tip. FIG. 9B shows that both leg members 60 and 70 are compressed at hinge points 73 and 74, respectively to clasp tightly about a tubular vessel 75 to close the lumen thereof, the compression being sufficient to provide permanent haemostapling of vessel 75. Both of the leg members lock each other at 69 and the tips 67 and 66 fix themselves in the tunica adventitia of the compressed blood vessel 75 at 72 and 71, respectively over side 61 as shown in FIGS. 9B and 9D. This mechanism of the present invention ensures that the haemo-staples are fixed firmly with the vessel therein and avoid slipping or giving away to ensure permanent haemostatis of the haemo-clipped or haemo-stapled vessels.

The haemo-staples of the present invention may be constructed in various sizes according to their intended function. Haemo-staples are typically less than 6 mm in length and 0.5 mm to 1 mm in width and have a vessel clamping face about 3 mm in length. The dimensions of the haemo-staple may be reduced by about 50% for certain applications in microsurgery and therefore, the entire instrument along with haemostapling device would be made in matching order. Larger haemo-staples for special haemostatic application and other functions such as closure of oviduct or vas deferens may have dimensions of about double of those of a typical haemostatic staple or clip or haemo-staple.

The various sizes of haemo-staples are preferably matched with their respective stapling scissors tailored in accordance with the haemo-staple selected for best performance. The haemo-staples employed for the scissors of the present invention are most conveniently made of cast or machined from solid polymeric plastic materials or from metals such as aluminum, magnesium, stainless steel, titanium and various alloys of these, some of which may also be absorbable in biological tissues. Preferred absorbable polymers include homopolymers and copolymers of glucolide and lactide and poly (P-dioxanone). Preferred nonabsorbable polymers include nylon and polypropylene. All these materials have been demonstrated to be biologically acceptable when used as sutures or other implantable medical devices.

Figure 10B:
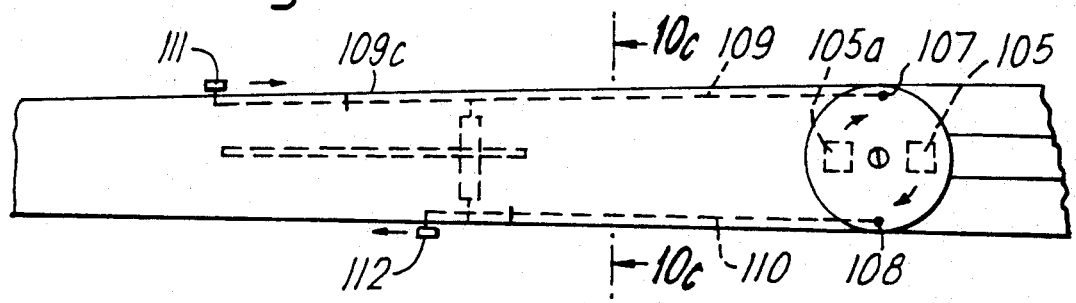
FIG. 10B shows in detail another view of the underside of the lower jaw member having the automatic blood vessel aligne mounted thereon.
Figure 10C:
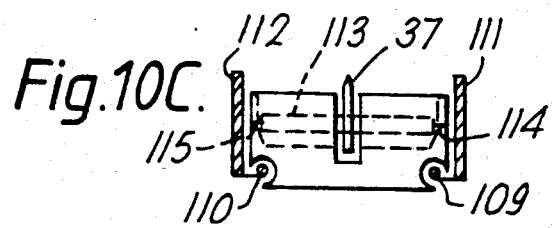
FIG. 10C shows a cross-section view along the direction of arrow C—C of FIG. 10B.
Figure 10D:
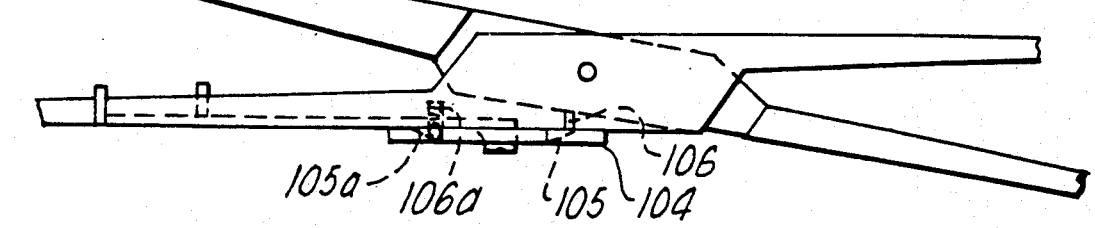
FIG. 10D is a plan view of the scissors in the direction of arrow D of FIG. 10A.
Figure 13:
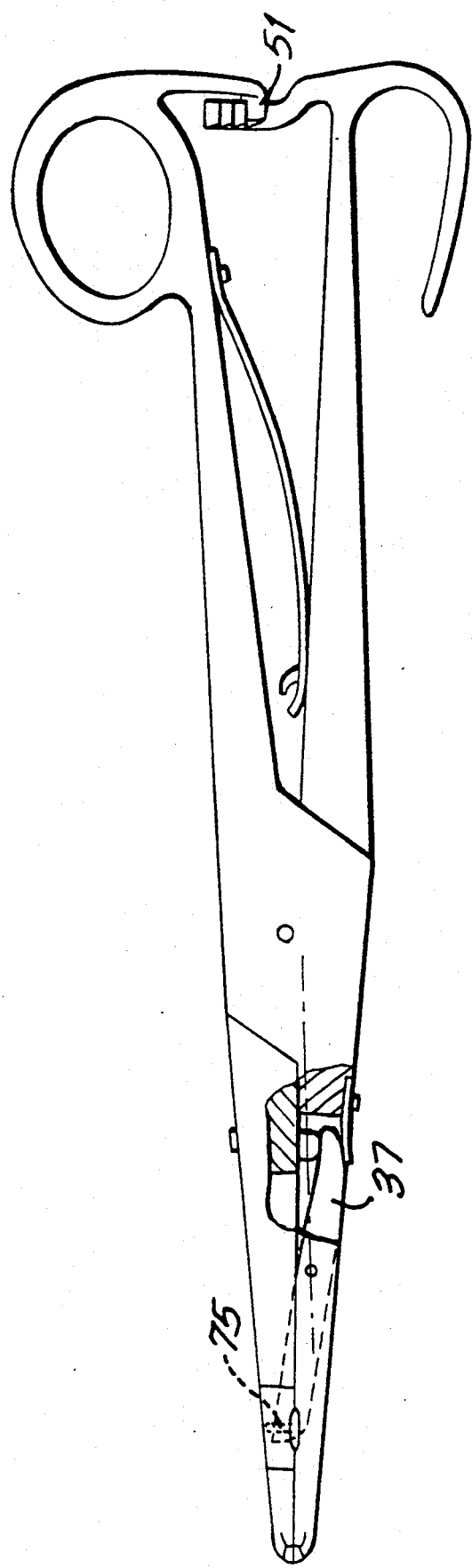
FIG. 13 is a top plan view of the scissors in the position in which the severed ends of the blood vessel are stapled.

In another embodiment, the cutting blade can be pivoted in the slot in any suitable manner as illustrated in figure 10C and 10E. For example, the blade 37 can be permanently held to a pivot axle 113 which can be a hollow rod or have hollow interiors at its two ends with a spring member housed in the hollow portion/portions. Engaging pins 114 and 115 are mounted on these spring members, which pins have a wider base housed within the hollow portion and an engaging extension projecting outside the hollow ends. The pins are secured in position by slightly narrowing the mouth ends to allow a free movement of the projecting ends. Complementary holes 116 are provided in the two walls of the lower jaw member and these two holes are in communication with small serrations formed on the lower jaw member. While mounting the blade, the two ends of the pivot axle are set on top of the two serrations and the pivot axle is slightly pressed down. The projecting engaging pins move slightly inside the hollow portions along the steep side wall 118 and 119 and at the same time slide down the serrations till the holes are reached. The two engaging pins are urged by the spring into the holes, and the pivot axle is now locked in position.

For removing the blade, the two engaging pins can be easily pushed inwards by means of a sharp pin applied from outside to disengage pins 114 and 115 from their respective holes and release them on the steep sidewalls 118 and 119; the pins slip upward along with the blade by virtue of spring tension acting laterally on them. The floating blade further may be discanted by any thumb forcep. In another embodiment shown in FIGS. 10A, 10B and 10C an arrangement for aligning the blood vessel on the blade can be provided operated automatically with the movement of the jaws. This arrangement is provided on the lower jaw member as a pivoted disc 104 mounted at the outer bottom side of the lower jaw. The disc is provided with a window 105 having an inclined surface which is engaged by a fulcrum pin 106 mounted on the lower handle portion of the jaw member, at the location where the box joint 44 is made. When the handle members move toward or away from one another the fulcrum pin acts on the inclined surface of the window thereby rotating the disc clockwise and anti-clockwise or vice versa depending on the nature of the inclination of the inclined surface. The disc carries two diametrically disposed pins 107,108 at the rim of the circumference of the disc 104 or on its flat surface, which are connected to two blood vessel engaging prongs 111 and 112 through connection wires 109 and 110 accommodated within suitable grooves 109c in the lower jaw member. The two grooves are shown in dotted lines in the drawings (see FIGS. 10C, 10A and 10B). Adjacent to the holding pins there are provided suitable surface serrations on the rim of the disc so as to accommodate the wire ends such that the wires are prevented from the lateral displacement.

The wire thus runs from the holding pin 107, sits on the serration, passes through the C-shaped hollow groove 19c, comes out of the groove at the farther end and is connected to the blood vessel engaging prong 111. The prong rests on the side of the lower jaw member, extends along with the same end and slightly protrudes above the inner flat surface of the lower jaw member. Similarly, the other wire 112 starts from the holding pin 108, lines on the serrations, runs through the groove 109C, comes out of the groove and terminates in the blood vessel engaging prong 112. This prong 112 also lies on the other side of the lower jaw member, extends vertically through the same and protrudes slightly above the inner flat surface of the lower jaw member at the other side. The fulcrum pin is provided in the region of the box joint on the lower handle and is in operational association with the window 105 of the disc 104. This window has an opening in the form of a slanting surface. When the jaw members are moved closer, the lower handle moves upward and beyond the fulcrum point, the fulcrum pin mounted on the lower handle part moves downwards engaging the slanted surface of the window 105. As the fulcrum pin moves through the window downwards, it rotates the disc either clockwise or anti-clockwise according to the angle of the slanting surface formed accordingly. Accordingly, the prongs 111 and 112 move towards one another (as shown in FIGS. 10A to 10H).

Since the prongs extend above the surface of the lower jaw member and the blood vessels lie on the surface of the lower jaw member, the prongs engage the blood vessels and move them towards the cutting blade 37 and align them exactly on the cutting edge of the blade and haemo-staples. Thus, when the two handles are pressed towards one another, the two jaw members move closer to each other, the two prongs move towards one another and the blood vessels are placed on the edge of the cutting blade and when further pressure is applied to the handles, the blood vessels are cut by the blade.

At this juncture, the second window 105a of the disc has shifted pari passu from its original position to a second position. In the original position of the second window, an opening in the second window is engaged by a spring-loaded ball lock 106a. As the second window shifts its position, the slanting surface therein guides over the ball, pressing it inwards against the action of the spring and keeps the ball under tension when the second window has shifted to the second position (see FIGS. 10F and 10G). The spring tension ball is all the time acting downwards on the slanting surface on the disc. When the pressure is released on the two handles and these are opened apart, the ball becomes released and under the action of the spring tension glides through the slanting surface of the window 105a while, simultaneously, the fulcrum pin 106 is automatically withdrawn from the first window. This happens until the ball is fully released and is locked in the hole of the second window. Thus, the two windows and the two slanting surfaces in these windows are properly constructed for this automatic alignment operation. It will thus be realized that when the handles are moved apart, the two prongs move away from each other from the cutting edge of blade. Thus, the prongs help in the exact alignment of the blood vessels on the cutting edge of the blade as well as haemo-staples.

OPERATION OF DISSECTING-CUM-HAEMOSTAPLING SCISSORS

The mechanism which maintains haemostasis-cutting ligation is devised internally into the upper and lower jaw members and it is adjusted in accordance with the pressure gradient between the fulcrum and the handle of the blade, in the upper and lower jaws respectively. The pressure gradient is applied by locks upon approximating both the handle members between the thumb and the ring fingers of the surgeon as explained above.

The tubular vessels or ducts to be severed are dessected out by means of sharp prongs of both jaw members from the rest of the tissues.

This arrangement is helpful in automatically aligning the blood vessels on the sharp edge of the cutting blade. For this purpose two prong members, one each disposed on either side of the flat inner surface of the lower jaw member, are operatively connected to a disc member rotatably mounted on the outside of the lower jaw member in the box-joint region and operated by a pin attached to the upper handle member.

Hameostatis is maintained by non-traumatic occlusion of vascular tissues caught between the non-traumatic haemostatic grooves of the upper and lower jaw members.

The built-in fulcrum in the upper jaw members moves into the aperture of the lower jaw member when both jaw members are engaged and the same exerts pressure on the handle of the blade downwards. The cutting edge of the blade rotates upwards into the slit-housing of the upper jaw member while slitting the stretched vessels between the non-traumatic haemostatic grooves of the jaw members. The cutting mechanism is based on shearing principle i.e. by the shearing movement of the positive side sharp edge of the blade against the edge of the slit-housing in the upper jaw member.

The continuous greater amount of pressure exerted by the fulcrum on the blade causes the staple-trigger to move upwards. As the blade end of the trigger rotates upwardly, the end of the haemo-staple moves downwards and exerts pressure on the back of the most proximal haemo-staple which is ejected downwards into the recesses of the lower jaw member. The continued pressure further forms the haemo-staple into the figure of horizontal "eight", clasping the cut ends of the tubular vessel into its folded leg members, which ensures permanent staple-ligation of the cut vessel.

The last lock of the lock-release system is designed to ensure an automatic release of the knob 51 of the upper handle by means of the tensile action of the spring between the handles. As soon as the upper and lower jaw members are open the action of the fulcrum from the blade handle is over, the latter returns, in situ, to the lower jaw member and the hameo-staple at both sides in the upper jaw member slides medially to become ready for the next use within seconds.

In an embodiment of the invention, only one haemo-staple magazine may be provided, having haemo-staples and mounted between the two jaw members close to the box-joint. In this embodiment, the inner sides of the two jaw members are formed with suitable depressions to form a housing for the haemo-staple magazine. The magazine is situated in the depression of the lower jaw member and is removably-fixed thereto. In close association with the magazine, the cutting blade is mounted as explained before. The inner edge of the box-joint-half of the upper jaw member is provided with a pair of haemo-staple pushing pins, each of which rests against a haemo-staple in the open position of the jaw members. When the jaw members are moved towards one another, the two haemo-staple pushing pins push a pair of most proximate haemo-staples from the staple magazine towards the cutting edge of the blade and position one on either side of the blade. The extreme ends of the depressions in the upper jaw member and lower jaw member are suitably provided with curved inner end surfaces so that the ends of the legs of the forward advancing haemo-staples abut against these surfaces. The blood vessel already lying on the cutting blade is positioned between the two legs. When the jaw members are moved further closer, the blood vessel is cut and the two leg members of the haemo-staple are now bent towards one another by the curved edges of the jaw surfaces, thereby pressing and locking the cut end of the blood vessel between the two leg members and the intermediate connecting body of the haemo-staple, as explained above.

FIG. 9 shows the scissors in an open position thereof. The staple magazines are press-fitted in the cavities provided in the upper jaw member, as has been described in connection with FIG. 2C.

As will be seen from FIG. 11, when the two handles are brought towards each other from the position of FIG. 9 and a first lock 52a of the locking system is engaged by the lock knob 51 the surfaces of both jaw members are in alignment. In conducting the operation, the surgeon locates the necessary blood vessel to be cut and brings it onto the inner surface of the lower jaw member and the blood vessel is brought to the region of the cutting blade by means of the blood vessel aligner 104 to 112. The blood vessel is aligned on the cutting edge of the blade and positioned vertically below the staple pins in the upper jaw member. Thus, the blood vessel is nipped between the jaw surfaces and positioned on the blade ready to be cut.

When the handles are brought closer the blade 37 is further pivoted; the cutting edge of the blade is lifted and in its upward movement it cuts the blood vessel which is held between the jaw member.

As can be seen from FIG. 12 which shows the second stage of the operation, at this stage, the second lock 52b of the locking system is engaged by the lock knob 51. When the two handles are brought closer even further the lug 14 in the upper jaw moves further down into the slit-housing 35 in the lower jaw member, pushing the free end of the blade 37 further downwards. The tip end of the pivoted blade 37 swings further upwards after having cut the blood vessel. The two severed ends of the blood vessel lie on the both sides of the central slit-housing of the lower jaw member and are nipped therein by the serrated surfaces of the jaw members. As the tip end of the blade 37 swings upward it engages the pivoted ends of two haemo-staple triggers 19, which extend across the top surface of the upper jaw member and whose other ends are bent downwards and lie on the staple pin. The tip end of the blade pivotally held in the lower jaw member makes a sweeping upward motion and lifts ends 19a of the two triggers 19, and their distal ends 19b with plates 19c press one staple pin 21 from either side of the upper jaw member and thus two staple pins 21 move downwards. At this stage, the two legs of each staple pin 21a,21b lie on either side of the blood vessel and the two ends of the legs of each haemo-staple pin rest on the recesses opposing 31a,31b, as can be seen in FIG. 3A. The legs of the staple pins are now bent as can be seen in FIGS. 9a,9b,9c and 9d. Thus, simultaneously, both severed ends of the blood vessel are clasped by one staple pin each. At this stage, the lock knob 51 passes through lock stages 52c and 52d. All the operations are now complete.

In order to release the jaw members, it is sufficient to push both handles further towards each other. When the lower end of the lock member 52d is reached, the upper handle, i.e. the handle of the lower jaw member, is automatically released because of the tension of the leaf spring 48.

We claim:

1. Dissecting-cum-haemostatic scissors comprising an upper jaw member and a lower jaw member hingedly connected to each other; said upper jaw member having a first extension merging into a lower handle member, said lower jaw member having a second extension merging into an upper handle member, said upper handle member having a ring portion at a rear end thereof, said ring portion being adapted to accommodate the thumb of a surgeon, a lower end of said ring portion having a lock knob adapted to engage a lock release system formed on an upper portion at a rear end of said lower handle member, said lock release system including a plurality of locks each adapted to engage said lock knob when two handle members are brought closer towards each other, said lock release system also including a final lock release member adapted to release the lock knob when the lock knob is brought face to face with said lock release member such that the upper handle member is released from the lower handle member to take an original position thereof; a handle spring provided between said upper handle member and said lower handle member and adapted to the two handle members to remain separated from each other, the rear end of the lower handle member having a support for accommodating the fingers of the surgeon, the upper jaw member and the lower jaw member each being provided with a sharp prong at an extreme forward end thereof, the lower jaw member having a flat inner surface provided with a longitudinal slit housing extending centrally of the same wherein said slit housing extends downwardly and is adapted to accommodate a pivotable sharp cutting blade therein, said blade having a cutting edge lying flush with the flat surface of the lower jaw member, and wherein said sharp blade is a disposable blade and has a blunt edged tip disposed at an outer end of said slit housing and is also provided with a handle extending towards an inner end of said slit housing, said handle of the blade being pivotally secured to said slit housing by a pivot pin forming a fulcrum point of the handle, a lower end of the handle of the blade being acted upon by a blade release spring provided at said slit housing, the upper jaw member having at an inner side thereof a fulcrum acting on the handle of the blade such that when the lower handle member and the upper handle member are brought towards one another, the upper jaw member and the lower jaw member are urged towards each other and the fulcrum on the inner side of the upper jaw member acts upon the handle of the blade to pivotally urge the blade upwards from the slit housing while, at the same time, the lock knob is in engagement with different locks of the lock release system successively; and a set of staple magazines containing haemostaples and being accommodated inside an intermediate portion of said upper jaw member, such that when a vascular tissue or a blood vessel to be operated upon is grasped by the scissors, the prongs of said upper and said lower jaw member operate to dissect and place the vascular tissue or blood vessel between the upper jaw member and the lower jaw member and position the same directly above the cutting blade and directly below a staple magazine such that when the upper and lower jaw members are urged towards each other, the vascular tissue or blood vessel is cut and also ends of a cut are subjected to haemo-stapling immediately after cutting automatically by haemo-staples accommodated int he staple magazine.

2. The scissors as claimed in claim 1, wherein an inner end of the slit housing of the lower jaw member is provided with a fulcrum aperture enabling said fulcrum to enter into said aperture and act upon the handle of the blade.

3. The scissors as claimed in claim 1, wherein said longitudinal slit housing in said lower jaw member is a through-slit, said blade release spring is a leaf spring plate mounted on an underside of the lower jaw member such that an underside of the handle of the blade extends through said slit housing and is acted upon by said leaf spring plate.

4. The scissors as claimed in claim 1, wherein said blade-release spring is a coil spring accommodated within the slit housing below an underside of the handle of the blade.

5. The scissors as claimed in claim 1, wherein U-shaped haemostatic grooves are provided in the lower jaw member, each groove having a curvature which extends beyond an outer end of said slit housing.

6. The scissors as claimed in claim 5, wherein the upper jaw member is provided with a longitudinal slit housing centrally thereof, said slit housing enclosing the cutting blade accommodated in the lower jaw member when said blade is pivotally urged above a surface of the lower jaw member when the upper and lower jaw members are brought closer towards each other.

7. The scissors as claimed in claim 6, wherein said longitudinal slit housing of the upper jaw member is provided with U-shaped non-traumatic haemostatic grooves corresponding to and matching the haemostatic grooves formed in the lower jaw member.

8. The scissors as claimed in claim 7, wherein said handle spring is a leaf spring with one end thereof held to an undersurface of one of the upper handle member and lower handle member, and another end of said spring being slideably engaged on another handle member.

9. The scissors as claimed in claim 8, wherein said another end of said leaf spring is provided with an indentation at an edge thereof and adapted to slidably engage a groove provided in an inner surface of the respective handle member.

10. The scissors as claimed in claim 7, wherein the handle spring is made of two leaf plate members, one end of each plate member being secured to one of the upper and lower handle members while free ends of said two plate members are in sliding contact with each other.

11. The scissors as claimed in claim 1, wherein said cutting blade is pivotally held on a hollow mounting bar which has two ends provided with two locking members urged by at least one spring held within a hollow of said mounting bar, said two locking members being adapted each to engage a hole provided in each of lateral sides of a groove of the lower jaw member and wherein said slit housing is provided with an extension to accommodate said hollow mounting bar therein.

12. The scissors as claimed in claim 1, wherein the lower jaw member is provided on an underside thereof with automatic blood vessel alignment means comprising a disc member mounted on the underside of the lower jaw member and being spaced from a hinge of the upper and lower jaw members, said disc member being rotatably held on said underside of the lower jaw member, said disc member being provided with two openings each having inclined surfaces, said inclined surfaces being inclined contrary to each other, one such opening and inclined surface being adapted to be engaged by a fulcrum pin mounted on the underside of the lower handle member, another opening being adapted to be in engagement with a spring-loaded ball catch housed within an opening at the underside of the lower jaw member, said disc member further including a pair of diametrically opposed pins positioned close to edges of an outer side of the lower jaw member, and a pair of blood vessel aligning prongs operatively connected to said pins by a pair of flexible wires.

13. The scissors as claimed in claim 12, wherein said inclined surface of said opening of said disc member is engaged by the fulcrum pin at such an angle that the fulcrum pin slides over the inclined surface and rotates the disc member clockwise as it further advances through the opening when the two handle members are brought close to each other.

14. The scissors as claimed in claim 13, wherein the inclined surface of another opening is provided at such an angle that when the disc member starts rotating clockwise when the fulcrum pin is urged through said one opening, the inclined surface slides over the ball catch housed underneath the opening pressing against the action of a spring.

15. The scissors as claimed in claim 12, wherein each of said two blood vessel aligning prongs is connected to a respective one of said two opposed pins by a flexible wire and wherein each of said wires is accommodated in a respective groove formed on the underside of the lower jaw member, each groove running along longitudinal edges of the outer side of the lower jaw member.

16. The scissors as claimed in claim 15, wherein said grooves extend to a substantial length from a place where the disc member is mounted and are formed as C-shaped grooves extending towards an end of the lower jaw member.

17. The scissors as claimed in claim 16, wherein the cutting blade is held on a pivot rod which is provided with a pair of spring-biased end pins such that the cutting blade and the pivot rod can be slid into a cavity provided in an inner side of the lower jaw member, said cavity having walls provided with suitable grooves for accommodating said two pins, and wherein said two grooves terminate in suitable holes in the walls of said cavity, said cavity having inclined wall surfaces toward the bottom to facilitate loading and unloading of the blade and the pivot rod.

18. The scissors as claimed in claim 1, wherein holding means formed as a recess is provided on the lower handle member, for accommodating a bipolar electrode of a cauterization unit, and wherein said bipolar electrode is made as a detachable plug and being of shape and size to fit said holding means and is fixed to a chord which is removably connected to the cauterization unit.

* * * * *